United States Patent [19]

Charping

[11] Patent Number: 4,818,759

[45] Date of Patent: Apr. 4, 1989

[54] TREATMENT OF DISEASE

[76] Inventor: Carol S. S. Charping, 521 Brookwood Dr., Durham, N.C. 27707

[21] Appl. No.: 152,837

[22] Filed: Feb. 5, 1988

[30] Foreign Application Priority Data

Feb. 6, 1987 [GB] United Kingdom ............... 8702758

[51] Int. Cl.$^4$ ........................................... A61V 31/505
[52] U.S. Cl. .................................................. 514/260
[58] Field of Search ........................................ 514/260

[56] References Cited

U.S. PATENT DOCUMENTS

| | | | |
|---|---|---|---|
| 3,322,765 | 5/1967 | Hitchings et al. | 544/279 |
| 4,372,957 | 2/1983 | Duch et al. | 424/251 |

FOREIGN PATENT DOCUMENTS

| | | |
|---|---|---|
| 1084103 | 1/1981 | European Pat. Off. . |
| 0021292 | 7/1981 | European Pat. Off. . |

OTHER PUBLICATIONS

British Medical Journal, vol. 292, 1986, pp. 431–432.

*Primary Examiner*—Stanley J. Friedman
*Attorney, Agent, or Firm*—Donald Brown

[57] ABSTRACT

A method of treatment of rheumatoid arthritis in humans in need thereof which comprises administering to said human an effective rheumatoid arthritis treatment amount of compound 2,4-diamino-6-(2,5-dimethoxybenzyl)-5-methylpyrido[2,3-d]pyrimidine or pharmaceutically acceptable acid addition salt thereof.

7 Claims, No Drawings

TREATMENT OF DISEASE

BACKGROUND OF THE INVENTION

The present invention relates to 2,4-diamino-6-(2,5-dimethoxybenzyl)-5-methylpyrido[2,3-d]pyrimidine or a pharmaceutically acceptable acid addition salt thereof for treatment of rheumatoid arthritis in a human suffering from rheumatoid arthritis.

UK. Pat. No. 1 084 103 (and corresponding U.S. Pat. No. 3,322,765) discloses 2,4-diaminopyrido[2,3-d]pyrimidines of the general formula (A):

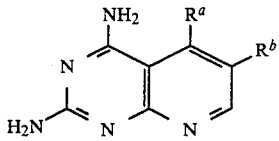

in which $R^a$ is hydrogen or alkyl and $R^b$ is inter alia an unsubstituted benzyl group or a benzyl group substituted by one or more halogen atoms, alkyl or alkoxy groups. The compounds of formula (I) were described as having high in vitro and in vivo activity against bacteria or bacterial infections in experimental animals.

Subsequently it has been found that the compounds of formula (A) specifically disclosed in U.K. Pat. No. 1 084 103 show some inhibitory activity against mammalian dihydrofolate reductase (DHFR), and the activity was sufficient to render them potentially useful in the treatment of conditions where inhibition of mammalian DHFR is desirable.

It has further been found that many of these compounds are potent inhibitors of histamine N-methyltransferase (HMT), an enzyme involved in the metabolism of histamine. In this manner they often cause an undesirable accumulation of histamine in organs and tissues. The effects of histamine are well known and any possibility of a further utility for these compounds was substantially diminished by their strong inhibition of HMT.

Further investigation showed that a number of other compounds of formula (I) also possessed DHFR inhibitory activity but that these, too, were also potent inhibitors of HMT. Others, which had acceptably low levels of inhibition of HMT were found to have insufficient activity as inhibitors of DHFR.

European patent specification No. 0021292 and U.S. Pat. No. 4,372,957 disclose that compounds of the formula (B):

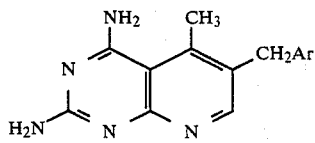

wherein Ar is

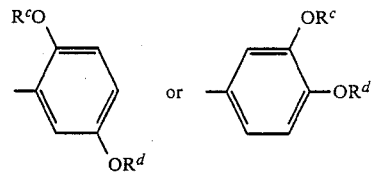

and $R^c$ and $R^d$ are lower ($C_{1-6}$) alkyl; and pharmaceutically acceptable acid addition salts thereof are not only very potent inhibitors of mammalian DHFR, but also have acceptably low inhibitory activity against HMT, and are useful in the treatment of proliferative diseases, such as psoriasis, basal and squamous cell carcinomas of the skin, and various forms of cancer including leukemias, lymphomas, sarcomas and solid tumors. Preferably monobasic salts are provided.

2,4-Diamino-5-methyl-6-(2,5-dimethoxybenzyl)-pyrido[2,3-d]pyrimidine is identified as a preferred compound.

The present invention concerns the use of 2,4-diamino-5-methyl-6-(2,5-dimethoxybenzyl)pyrido[2,3-d]pyrimidine in the treatment of rheumatoid arthritis.

Thus, in one aspect the present invention is directed to the administration of a compound of formula (I),

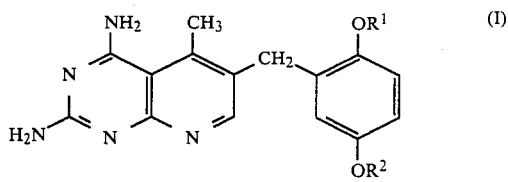

wherein $R^1$ and $R^2$ are each alkyl of 1 to 4 carbons, or a pharmaceutically acceptable acid addition salt thereof to a human for the treatment of rheumatoid arthritis in a human in need thereof (i.e. a human who has been diagnosed as having the disease rheumatoid arthritis).

In a further aspect the invention provides a compound of formula (I) for use in the treatment of rheumatoid arthritis.

In a yet further aspect the present invention provides a compound of formula (I) for use in the manufacture of a medicament for the treatment of rheumatoid arthritis.

Most preferred for use according to the present invention is the compound of formula (I) wherein $R^1$ and $R^2$ are each methyl; this preferred compound is also named 2,4-diamino-6-(2,5-dimethoxybenzyl)-5-methylpyrido[2,3-d]pyrimidine.

The medicinal activity of the compound of formula (I) resides in the free base. The nature of the acid participating in the acid additions salts is of minor importance except in so far as it affects solubility and bioavailability. Such acid addition salts include, for example, those derived from hydrochloric acid, hydriodic acid, sulphuric aicd, phosphoric acid, acetic acid, p-toluenesulphonic acid, methanesulphonic acid, maleic acid, lactic acid, citric acid, tartartic acid, succinic acid, p-chlorobenzenesulphonic acid, isethionic acid, glucuronic acid, pantothenic acid and lactobionic acid. Preferably the salt is mono-basic salt. The most preferred salt is the isethionate.

As used herein rheumatoid arthritis is defined as a chronic systemic disease of unknown etiology in which symptoms and inflammatory connective-tissue changes predominate in articular and related structures. Pain, limitation of motion and joint deformity are common. Common synonyms for the term rheumatoid arthritis are atropic arthritis, chronic infectious arthritis and proliferative arthritis. The term treatment of rheumatoid arthritis as used herein also includes treatment of rheumatoid spondylitis, a chronic progressive arthritis affecting the spine and sacroiliac joints, as well as psoriatic arthritis by administering a compound of formula (I) or a pharmaceutically acceptable acid addition salt thereof to a human in need thereof.

The compound of formula (I) or its pharmaceutically acceptable acid addition salts may be prepared by any method known in the art for the preparation of compounds of analogous structure, for example as described in the aforementioned European patent specification No. 21292.

Whilst it is possible for the compound of formula (I) and salts thereof to be utilised according to the present invention in the form of the raw chemical, they are preferably presented in the form of a pharmaceutical formulation.

The present invention thus also provides the use of a pharmaceutical formulation comprising as the active ingredient a compound of formula (I) or its pharmaceutically acceptable acid addition salt together with a pharmaceutically acceptable carrier thereof in the treatment of rheumatoid arthritis in a human.

Methods for the preparation of a pharmaceutical formulation are well known in the art and comprise bringing into association an active compound, i.e. a compound or salt of formula (I), and a pharmaceutically acceptable carrier therefor.

Pharmaceutical formulations for use in this invention include those suitable for oral, rectal, topical and parenteral administration although of those oral formulations are preferred. The formulations may, where appropriate, be conveniently presented in discrete dosage units and may be prepared by any of the methods well known in the art of pharmacy. A convenient unit dose formulation contains the active compound in amount of from about 1 mg to about 1 g, preferably about 2 mg to about 500 mg, most preferably about 10 mg to 100 mg, to be taken once or several times daily.

All methods for the preparation of such formulations include the step of bringing into association the active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules, cachets or tablets each containing a predetermined amount of the active compound. A tablet may be made by compression or moulding, optionally with one or more accessory ingredients. Compressed tablets may be prepared by compressing in a suitable machine the active compound in a free-flowing form such as a powder or granules optionally mixed with a binder, lubricant, inert diluent, lubricating, surface active or dispersing agent. Moulded tablets may be made by moulding in inert liquid diluent. Tablets may be optionally coated and, if uncoated, may be optionally scored. Capsules may be prepared by filling the active compound ingredients into the capsules cases and then sealing them in the usual manner. Slow or sustained release formulations are also suitable for practice of this invention. Cachets are analogous to capsules wherein the active ingredient together with any accessory ingredient(s) are sealed in a rice paper envelope.

Pharmaceutical formulations suitable for oral administration wherein the carrier is a liquid may be presented as a solution or a suspension in an aqueous liquid, or as an oil-in-water or water-in-oil liquid emulsion.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Pharmaceutical formulations suitable for parenteral administration include sterile solutions or suspensions of the active compound in aqueous or oleaginous vehicles. Such preparations are conveniently presented in unit dosage or multi-dose containers which are sealed after introduction of the formulation until required for use.

Pharmaceutical preparations for topical administration include a compound or salt of formula (I) together with a suitable vehicle, e.g., preferably one which promotes the passage of the compound or salt through the skin, or a patch containing the compound for application to the skin so that the compound or salt may penetrate the human skin.

It should be understood that in addition to the aforementioned carrier ingredients the pharmaceutical formulations described above may include, as appropriate, one or more additional carrier ingredients such as diluents, buffers, flavouring agents binders, surface active agents, thickeners, lubricants, preservatives (including anti-oxidants) and the like, and substances included for the purpose of rendering the formulation isotonic with the blood of the intended recipient.

As has been described above the compound of the present invention and its salts are useful for the treatment of rheumatoid arthritis. The invention thus provides a method for the treatment of rheumatoid arthritis disease in humans which comprises the administration of an effective amount of a compound of formula (I) or an acid addition salt thereof once or several times a day to a human having rheumatoid arthritis.

The amount of a compound of formula (I) required for therapeutic effect to treatment rheumatoid arthritis will of course vary with such factors as the severity of the disease, the age and weight of the patient, the route of administration, and where the compound is employed in salt form, the nature of the salt. In general, a suitable dose for the treatment of mammals (including humans) will lie in the range of from about 0.1 to 150 mg per kilogram body weight (mg/kg) per day, preferably in the range from of about 0.3 to about 50 mg/kg, more preferably in the range of about 0.5 to 20 mg/kg in terms of base. For acute treatment of rheumatoid arthritis a suitable regimen may be for example 2 to 5 mg/kg twice a day for 5 days. For chronic treatment a suitable dose may be for example 0.1 to 0.6 mg/kg one to four times per day for 21 days. All doses (amounts) are in terms of the free base.

Toxic manifestions attributable to active compound are typically those associated with folate depletion, such as bone marrow depression, megaloblastic changes, and gastrointestinal ulceration. Calcium leucovorin (calcium salt of 5-formyl-5,6,7,8-tetrahydrofolic acid) may be administered to effect reversal of these manifestations or to prevent their occurrence. The administration of calcium leucovorin may be effected concurrently with treatment or at any stage thereof whenever toxic symptoms appear.

Thus, the haematological activity of the active compound can be prevented or reduced by the simultaneous administration of calcium leucovorin.

Consequently, tissue levels of the active compound may be safely raised by increasing the dose of the compound together with a simultaneous administration of leucovorin.

Reference should be had to the following for background information:
1. British Medical Journal, Vol. 292, p. 431–432—Treatment of Severe Rheumatoid Arthritis—Feb. 15, 1986.
2. The Journal of Rheumatology, 12: 5, p. 904–905—Studies of Effect of Low Dose Methotrexate on Rat Adjuvant Arthritis—1985.
3. Arthritis and Rheumatism, Vol. 29, No. 7—Methotrexate Metabolism Analysis in Blood and Liver of Rheumatoid Arthritis Patients—July 1986.

The following Examples, which illustrate the invention, should in no way be construed as constituting a limitation thereof.

EXAMPLE 1

2,4-Diamino-5-methyl-6-(2,5-dimethoxybenzyl)-pyrido[2,3-d]pyrimidine

A mixture of 2,5-dimethoxybenzaldehyde (100 g), ethyl acetoacetate (84.5 g), anhydrous benzene (200 ml), piperidine (6 ml) and acetic acid (12 ml) was heated at reflux for 3 hours in an apparatus fitted with a Dean-Stark trap to collect the azeotropically distilled water. The reaction mixture was cooled, benzene (300 ml) added, and the solution was washed successively with water (100 ml), cooled 0.1N hydrochloric acid (200 ml), 5% aqueous sodium bicarbonate (200 ml) and dilute acetic acid (100 ml) and dried over anhydrous magnesium sulfate. The solvent was then removed under reduced pressure and the residual oil distilled, b.p. 169°–170° C./0.3 mm Hg. The product, ethyl α-(2,5-dimethoxybenzylidene)acetoacetate, solidified on standing (104 g, m.p. 68°–69° C.) and was recrystallised from ethanol-pentane (m.p. 72°–73° C.). A portion (38 g) of the product was reduced catalytically in the presence of palladium on charcoal catalyst (Pd/C) in ethyl acetate (150 ml). The product, after removal of solvent, was purified by distillation under reduced pressure to give ethyl α-(2,5-dimethoxybenzyl)acetoacetate, b.p. 146°–148° C./0.3 mm Hg.

A mixture of ethyl α-(2,5-dimethoxybenzylacetoacetate (21.2 g) 2,4,6-triaminopyrimidine (10 g) and diphenylether (100 ml) was heated at 190°–230° C. for 1.5 hours in an apparatus fitted with a Dean-Stark trap and water-ethanol (4 ml) was collected. Methanol (200 ml) and ethanol (50 ml) were added to the cooled reaction mixture. The resulting solid was collected by filtration and treated with boiling water (1 l) to give 2,4-diamino-5-methyl-6-(2,5-dimethoxybenzyl)-7-oxo-7,8-dihydropyrido[2,3-d]pyrimidine (17 g), m.p. 325°–326° C.

2,4-diamino-5-methyl-6-(2,5-dimethoxybenzyl)-7-oxo-7,8-dihydropyrido[2,3-d]pyrimidine (8 g) was chlorinated by treatment with Vilsmeier reagent prepared by slowly adding thionyl chloride (28.5 ml) in dry chloroform (25 ml) to a solution of dimethyl formamide (17.5 ml) in chloroform (100 ml) at 0°–5° C. The cold mixture of the pyridopyrimidine and Vilsmeier reagent was stirred, gradually allowed to reach ambient temperature, and then heated at reflux for 3 hours. It was then treated with ethanolic base (80 ml) maintaining the temperature at 25°–30° C. with cooling. The brown product formed was isolated, treated further with aqueous ammonia and then recrystallised from ethanol to give 2,4-diamino-5-methyl-6-(2,5-dimethoxybenzyl)-7-chloropyrido[2,3-d]pyrimidine, m.p. 193°–196° C. (dec.).

The chloro compound (0.3 g) was dissolved in ethanol (200 ml) containing potassium hydroxide (0.2 g). Palladium on charcoal catalyst (0.2 g) was added and hydrogenation commenced. Reduction was complete after 48 hours and yielded 2,4-diamino-5-methyl-6-(2,5-dimethoxybenzyl)pyrido[2,3-d]pyrimidine, m.p. 252°–254° C.

EXAMPLE 2

| Injectable | Amount |
| --- | --- |
| 2,4-Diamino-5-methyl-6-(2,5-dimethoxybenzyl)-pyrido[2,3-d]pyrimidine isethionate | qs to 5 mg/ml |
| Propylene glycol | 40 ml |
| Ethanol | 11 ml |
| Water for Injection | 49 ml |

EXAMPLE 3

| Injectable | Amount |
| --- | --- |
| 2,4-Diamino-5-methyl-6-(2,5-dimethoxybenzyl)-pyrido[2,3-d]pyrimidine isethionate | qs to 5 mg/ml |
| Propylene glycol | 40 ml |
| 5% Dextrose solution | 60 ml |

EXAMPLE 4

| Tablet | Amount |
| --- | --- |
| 2,4-Diamino-5-methyl-6-(2,5-dimethoxybenzyl)-pyrido[2,3-d]pyrimidine isethionate | 50 mg |
| Lactose | 85 mg |
| Potato starch, dried | 14.3 mg |
| Magnesium Stearate | 0.7 mg |

EXAMPLE 5

| Capsule | Amount |
| --- | --- |
| 2,4-Diamino-5-methyl-6-(2,5-dimethoxybenzyl)-pyrido[2,3-d]pyrimidine isethionate | 5 mg |
| Lactose | 50 mg (in a two part gelatin capsule) |

EXAMPLE 6

Preparation of Salt of Isethionate Acid

Compound of formula (I) wherein $R^1 = R^2 = CH_3$ (488 g) and ethanol (6.0 l) was stirred at 77°–78° C. and isethionic acid (208.1 g in a concentrated aqueous solution containing about 6.3 meg. isethionic acid per gram of solution) was added. The reaction mixture was continuously stirred and cooled to 40° C. over one hour. The resulting slurry was cooled to 5° C. for two hours, filtered and washed with ethanol (0.5 l). The crude product was dissolved in hot ethanol-water, treated with charcoal, filtered, and the solution then chilled to 5° C. to crystallise the product. Yield: 583 grams of 2,4-diamino-5-methyl-6-(2,5-dimethoxybenzyl)-pyrido[2,3-d]pyrimidine isethionate, m.p. 220°–223° C.

EXAMPLE 7

Activity of 2,4-Diamino-5-methyl-6-(2,5-dimethoxybenzyl)-pyrido[2,3-d]pyrimidine The compounds were administered in the ground meal diet to rats for 14 days beginning on the day of sensitization with Freund's adjuvant according to the procedure described in *J. Immunopharmacology*, 1 (4), 497 (1979). The severity of the polyarthritis was evaluated on the 16th day after sensitization by a global assessment of the degree of edema, erythema, scaling and nodules in the joints and tail as described in *J. Exp. Med.*, 121, 185 (1968). The $ED_{50}$ values tabulated below represent the doses of the indicated compounds that produced a 50% reduction of the average global arthritic joint score relative to a control group.

| Compound | $ED_{50}$ (mg/kg) |
| --- | --- |
| 2,4-Diamino-5-methyl-6-(2,5-dimethoxybenzyl)pyrido[2,3-d]pyrimidine isethionate | 19 |
| Aspirin | 102 |

I claim:

1. A method of treating rheumatoid arthritis in a human suffering from rheumatoid arthritis comprising the admnistration of an effective anti-rheumatoid arthritis treatment amount of a compound of formula (I):

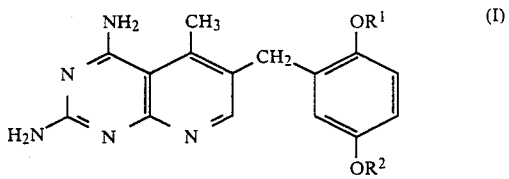

wherein $R^1$ and $R^2$ are each alkyl of 1 to 4 carbons or a pharmaceutically acceptable acid addition salt thereof to said human.

2. A method according to claim 1 in which 2,4-diamino-6-(2,5-dimethoxybenzyl)-5-methylpyrido[2,3-d]pyrimidine is administered to said human.

3. A method according to claim 1 in which the isethionate salt of 2,4-diamino-6-(2,5-dimethoxybenzyl)-5-methylpyrido[2,3-d]pyrimidine is administered to said human.

4. The method according to claim 1 in which the compound or salt is administered orally to said human.

5. The method according to claim 1 in which the salt is administered orally to said human.

6. The method according to claim 3 in which the isethionate salt is administered orally to said human.

7. The method of claim 6 in which the salt is administered orally as part of a tablet or in a capsule.

* * * * *